United States Patent [19]

Gravener et al.

[11] Patent Number: 5,360,417
[45] Date of Patent: Nov. 1, 1994

[54] VALVE ASSEMBLY FOR INTRODUCING INSTRUMENTS INTO BODY CAVITIES

[75] Inventors: Roy D. Gravener, Fairfield; Alex Lanniruberto, Waterbury, both of Conn.; Michael Ciccolella, Lake Carmel, N.Y.

[73] Assignee: United States Surgical Corporation, Norwalk, Conn.

[21] Appl. No.: 167,230

[22] Filed: Dec. 14, 1993

Related U.S. Application Data

[63] Continuation of Ser. No. 874,291, Apr. 24, 1992, abandoned.

[51] Int. Cl.$^5$ ............................................. A61M 31/00
[52] U.S. Cl. ...................................... 604/278; 604/31; 604/169; 604/246; 251/5
[58] Field of Search ................... 604/30, 31, 34, 167, 604/169, 246, 249–250, 256, 278; 251/4, 5, 11

[56] References Cited

U.S. PATENT DOCUMENTS

| | | |
|---|---|---|
| 729,423 | 5/1903 | Scheiber et al. . |
| 2,797,837 | 7/1957 | Roberts . |
| 3,086,797 | 4/1963 | Webb . |
| 3,197,173 | 7/1965 | Taubenheim . |
| 3,438,607 | 4/1969 | Williams et al. . |
| 3,565,448 | 4/1969 | Angelbeck . |
| 3,811,440 | 5/1974 | Moorehead et al. . |
| 3,856,010 | 12/1974 | Moorehead et al. . |
| 3,875,938 | 4/1975 | Mellor . |
| 3,920,215 | 11/1975 | Knauf . |
| 3,970,089 | 7/1976 | Saice . |
| 3,977,400 | 8/1976 | Moorehead . |
| 3,994,287 | 11/1976 | Turp et al. . |
| 4,000,739 | 1/1977 | Stevens . |
| 4,149,535 | 4/1979 | Volder . |
| 4,177,814 | 12/1979 | Knepshield et al. . |
| 4,231,400 | 11/1980 | Friedling et al. . |
| 4,240,411 | 12/1980 | Hosono . |
| 4,243,034 | 1/1981 | Brandt . |
| 4,303,100 | 12/1981 | Kalb ................................. 137/853 |
| 4,324,239 | 4/1982 | Gordon et al. . |
| 4,378,013 | 3/1983 | LeFevre . |
| 4,424,833 | 1/1984 | Spector et al. . |
| 4,473,369 | 9/1984 | Lueders et al. . |
| 4,475,548 | 9/1984 | Muto . |
| 4,496,348 | 1/1985 | Genese et al. . |
| 4,580,573 | 4/1986 | Quinn . |
| 4,610,665 | 9/1986 | Matsumoto et al. . |
| 4,610,674 | 9/1986 | Suzuki et al. . |
| 4,626,245 | 12/1986 | Weinstein . |
| 4,634,421 | 1/1987 | Hegemann . |
| 4,654,030 | 3/1987 | Moll et al. . |

(List continued on next page.)

FOREIGN PATENT DOCUMENTS

| | | |
|---|---|---|
| 0144699 | 10/1984 | European Pat. Off. . |
| 0344907 | 12/1989 | European Pat. Off. . |
| 0350291 | 1/1990 | European Pat. Off. . |
| 0517248 | 6/1992 | European Pat. Off. . |
| 7004051 | 7/1970 | Germany . |
| 3242870 | 6/1983 | Germany . |
| 2019219 | 10/1979 | United Kingdom . |

OTHER PUBLICATIONS

Raychem Product Design, Surgiport Seal blueprint, Oct. 23, 1990.

*Primary Examiner*—C. Fred Rosenbaum
*Assistant Examiner*—Corrine Maglione

[57] ABSTRACT

A valve assembly adapted for introduction of surgical instruments into a patient's body includes a valve body formed of a flexibly resilient material which defines an aperture for reception of the instrument. The aperture is configured and dimensioned such that insertion of the instrument into the aperture will cause the resilient material of the valve body to resiliently engage the outer surface of the instrument in a substantially gas tight manner. The valve assembly includes a biasing member for closing the valve body to form a gas tight seal prior to inserting the instrument therethrough.

8 Claims, 12 Drawing Sheets

U.S. PATENT DOCUMENTS

| | | |
|---|---|---|
| 4,655,752 | 4/1987 | Honkanen et al. . |
| 4,655,762 | 4/1987 | Rogers ................................. 604/403 |
| 4,673,393 | 6/1987 | Suzuki et al. . |
| 4,723,550 | 2/1988 | Bales et al. . |
| 4,783,045 | 11/1988 | Tartaglino ........................ 251/61.1 |
| 4,786,028 | 11/1988 | Hammond . |
| 4,798,594 | 1/1989 | Hillstead . |
| 4,817,631 | 4/1989 | Schnepp-Pesch et al. . |
| 4,839,471 | 6/1989 | Clark et al. . |
| 4,842,591 | 6/1989 | Luther . |
| 4,869,717 | 9/1989 | Adair . |
| 4,874,377 | 10/1989 | Newgard et al. . |
| 4,895,346 | 1/1990 | Steigerwald . |
| 4,895,566 | 1/1990 | Hillstead . |
| 4,909,798 | 3/1990 | Fleischhacker et al. . |
| 4,917,668 | 4/1990 | Haindl . |
| 4,929,235 | 5/1990 | Merry et al. . |
| 4,943,280 | 7/1990 | Lander . |
| 4,960,259 | 10/1990 | Sunnanväder et al. . |
| 4,960,412 | 10/1990 | Fink . |
| 4,978,341 | 12/1990 | Neiderhauser . |
| 5,000,745 | 3/1991 | Guest et al. . |
| 5,009,391 | 4/1991 | Steigerwald . |
| 5,009,643 | 4/1991 | Reich et al. . |
| 5,041,095 | 8/1991 | Littrell . |
| 5,053,014 | 10/1991 | Van Heugten . |
| 5,071,411 | 12/1991 | Hillstead ............................. 604/246 |
| 5,098,396 | 3/1992 | Taylor et al. ....................... 604/169 |
| 5,104,389 | 4/1992 | Deem et al. . |
| 5,127,626 | 7/1992 | Hilal et al. . |
| 5,180,373 | 1/1993 | Green et al. ........................ 604/167 |
| 5,201,714 | 4/1993 | Gentelia et al. . |

VALVE ASSEMBLY FOR INTRODUCING INSTRUMENTS INTO BODY CAVITIES

This is a continuation of copending application Ser. No. 07/874,291 filed on Apr. 24, 1992, now abandoned.

BACKGROUND OF THE INVENTION

1. Field of the Invention

This invention relates to valve systems of the type adapted to allow the introduction of a surgical instrument into a patient's body. In particular, the invention is applicable to a cannula assembly wherein a cannula extends from the valve assembly and is intended for insertion into a patient's body to accommodate an instrument inserted through the cannula and valve.

2. Background of the Prior Art

In laparoscopic procedures surgery is performed in the interior of the abdomen through a small incision; in endoscopic procedures surgery is performed in any hollow viscus of the body through narrow tubes or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. Moreover, laparoscopic and endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a trocar assembly comprised of a cannula assembly and an obturator. The cannula assembly includes a cannula tube attached to a valve assembly which is adapted to maintain a seal across the opening of the cannula assembly. Since the cannula tube is in direct communication with the internal portion of the valve assembly, insertion of the cannula tube into an opening in the patient's body so as to reach the inner abdominal cavity must maintain a relatively gas-tight interface between the abdominal cavity and the outside atmosphere.

Since surgical procedures in the abdominal cavity of the body require insufflating gases to raise the cavity wall away from vital organs, the procedure is usually initiated by use of a Verres needle through which a gas such as $CO_2$ is introduced into the body cavity. Thereafter, the pointed obturator of the trocar assembly is inserted into the cannula assembly and used to puncture the abdominal cavity wall. The gas provides a slight pressure which raises the inner wall surface away from the vital organs thereby avoiding unnecessary contact with the organs by the instruments inserted into the cannula. Following removal of the obturator, laparoscopic or endoscopic surgical instruments may then be inserted through the cannula assembly to perform surgery within the abdominal cavity.

In view of the need to prevent leakage of the insufflation gas from the cavity, the cannula is typically provided with a valve assembly which permits introduction of surgical instruments to provide selective communication between the inner atmosphere of the cavity with the outside atmosphere. In this regard, there have been a number of attempts in the prior art to provide such a seal as part of the cannula assembly.

One form of cannula assembly includes a flapper valve which is pivotally mounted within the cannula assembly and is automatically opened by the obturator or other object when it is inserted into the proximal end of the cannula. Conventional flapper valves may also be manually opened by pivoting a lever on the exterior of the cannula housing. See, e.g., U.S. Pat. No. 4,943,280 to Lander. Trumpet valves are also known.

U.S. Pat. No. 4,655,752 to Honkanen et al. discloses a cannula including a housing and first and second seal members. The first seal member is conically tapered towards the bottom of the housing and has a circular opening in its center, while the second seal member is cup-shaped and also possesses a conically tapered bottom end. The second seal member includes at least one slit in the center of the conically tapered bottom end to allow for passage of instruments.

U.S. Pat. No. 4,978,341 to Niederhauser discloses an introducer valve for a catheter in which an elastomeric valve body is provided with a central longitudinal opening. The valve body has an inner wall tapering inwardly to a central opening, and an outer wall which also tapers inwardly generally parallel with the inner wall. A ring may circumscribe the center of the valve body to bias the central opening into a closed position.

Although attempts have been made to provide a valve assembly which maintains the integrity of the seal between the body cavity and the atmosphere outside the patient's body, seal systems provided to date have failed to address the full range of surgeons' needs, especially when instruments varying in diameter are used.

The present invention provides a valve assembly which may be incorporated into a cannula assembly or utilized in combination with any type of tubular member for introduction into the body of a patient while permitting introduction of instruments through the valve assembly into the body. At all times, the surgeon maintains control over the interface between the atmospheres within and without the patient's body. Moreover, the present invention makes it possible to introduce instruments of varying sizes into the body and insures the maintenance of a gas seal despite instrument manipulation therethrough.

SUMMARY OF THE INVENTION

A valve assembly is provided for permitting introduction of an elongated object, typically of circular cross-section, such as a surgical instrument into a patient's body through a tube such as a cannula. The valve assembly includes a valve body formed of a flexibly resilient material which defines an aperture for reception of the object. The aperture is configured and dimensioned such that insertion of the object into the aperture will cause the flexible material defining the aperture to resiliently engage the outer surface of the object in a substantially gas tight manner. The valve assembly may further include a member for biasing the flexible material to a configuration whereby the aperture is normally closed to form a gas tight seal prior to inserting the object therethrough.

BRIEF DESCRIPTION OF THE DRAWINGS

The forgoing features of the present invention will become more readily apparent and will be understood by referring to the following detailed description of preferred embodiments of the invention, which are described hereinbelow with reference to the drawings wherein.

DETAILED DESCRIPTION OF THE PREFERRED EMBODIMENTS

The present invention contemplates introduction into a patient's body of all types of surgical instruments including, but not limited to clip appliers, lasers, photographic devices, graspers, scissors, tubes, and the like. All of such objects are referred to herein as "instruments".

Referring now in detail to the drawings, in which like reference numerals identify identical or similar elements, FIGS. 1-5 illustrate a valve assembly 10 which includes body 12 fabricated from a flexibly resilient material, e.g., a thermoplastic elastomeric polymer such as Kraton D, a styrene-butadiene elastomer available from Shell Chemical Co.. The body 12 defines a substantially central longitudinal aperture 14 which is designed and configured to receive an endoscopic portion of an instrument. The body 12 further includes a proximal end portion 16, and a distal end portion 18 which is elongated and substantially cylindrical in shape. The distal end portion 18 further includes a distal edge 20 whose significance will be discussed below. The proximal end portion 16 includes an opening 22, a wall plate 24, and an inwardly tapered neck portion 26. The body 12 further includes a middle portion 28 having substantially cylindrical walls. The axial length of middle portion 28 is typically from about 5 mm to about 4 cm, and preferably about 1.5 to 3 cm.

Figure 1:
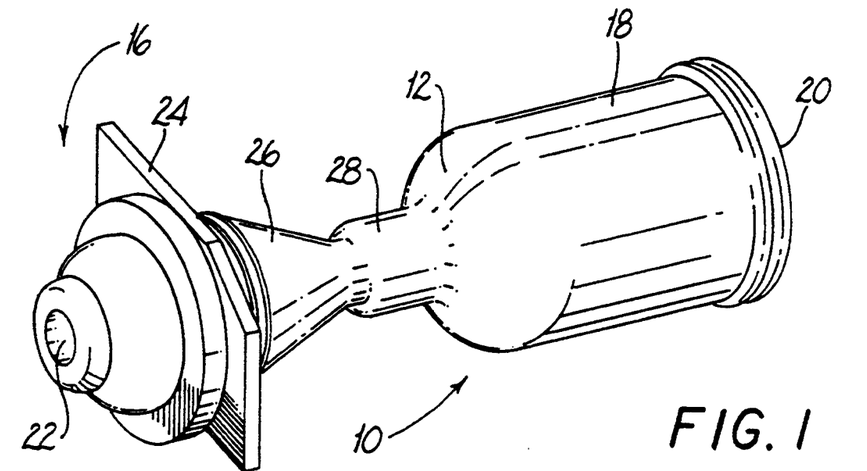
FIG. 1 is a perspective view illustrating a valve assembly according to the present invention.
Figure 2:
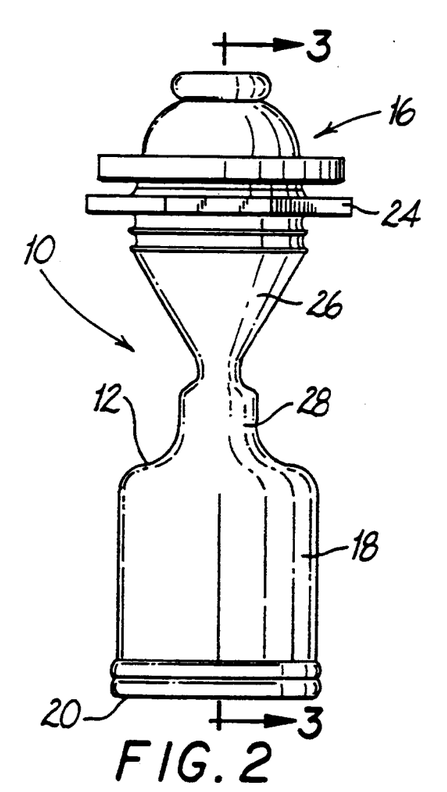
FIG. 2 is a side elevational view illustrating the valve assembly of FIG. 1.
Figure 3:
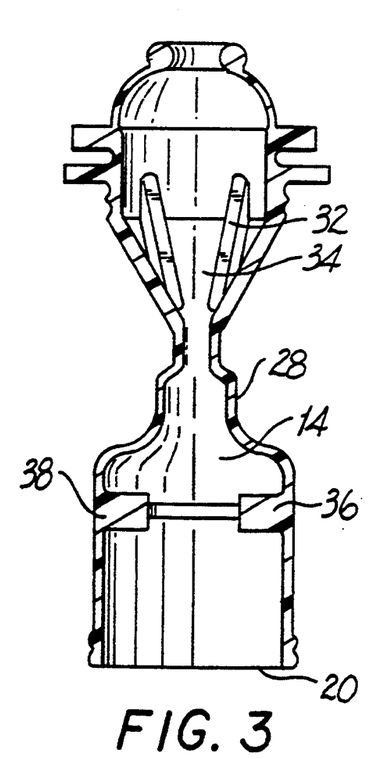
FIG. 3 is a cross-sectional view along line 3—3 of FIG. 2.

Referring to FIG. 3, the proximal end portion 16 further includes a plurality of splines 32 attached to an inner wall 34 and preferably integrally molded as part of inner wall 34. Alternatively, splines 32 may be insert molded and may include rigid members below the surface of inner wall 34, e.g., metallic strips or the like. The splines 32 extend in a generally longitudinal direction to assist in the insertion of an instrument into the neck portion 26 by reducing friction and drag forces associated therewith. Further, the splines 32 substantially prevent unwanted contact between the instrument and the inner wall 34 of the neck 26 that may injure or puncture the body 12. The distal portion 18 of the body 12 includes an inlet port 36 and an outlet port 38 whose function will be described below.

Figure 4:
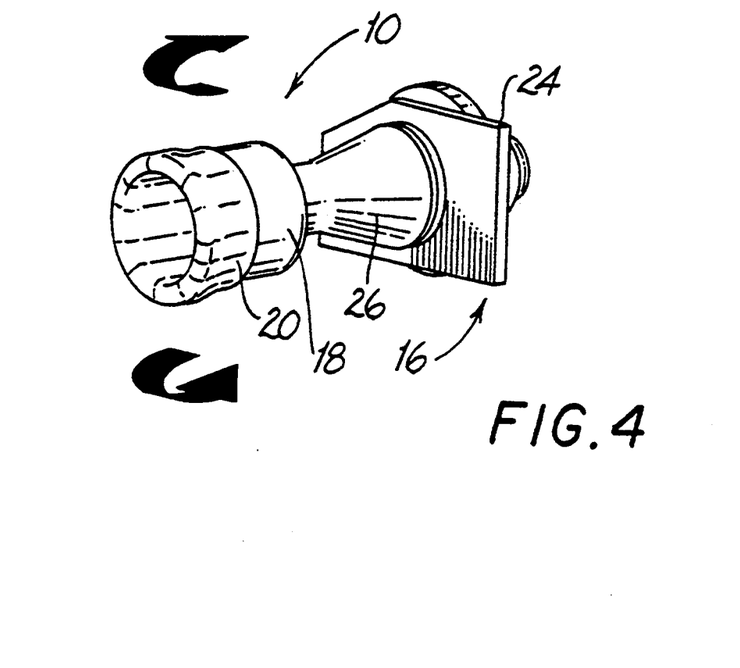
FIG. 4 is a perspective view illustrating an assembly step of the valve assembly of FIG. 1.
Figure 5:
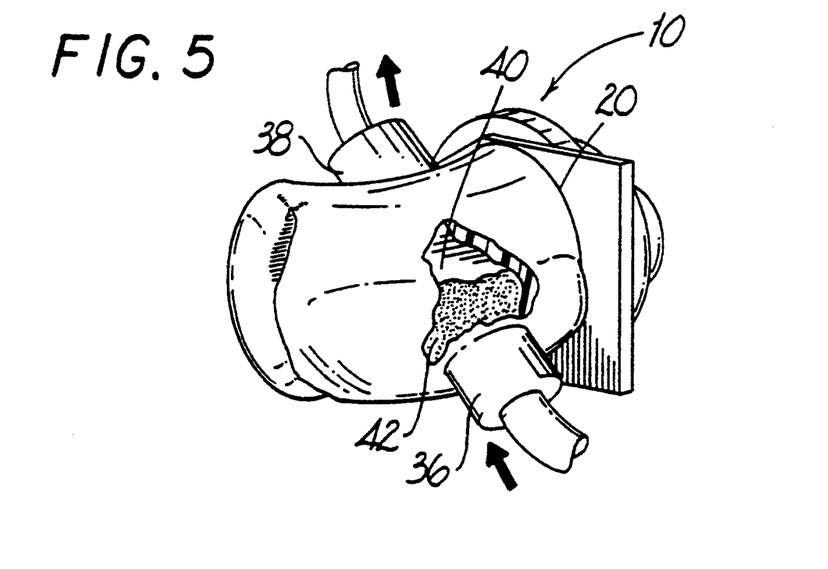
FIG. 5 is a perspective partial cut-away view illustrating introduction of fluid into the valve assembly to provide compressive biasing of the valve.
Figure 6:
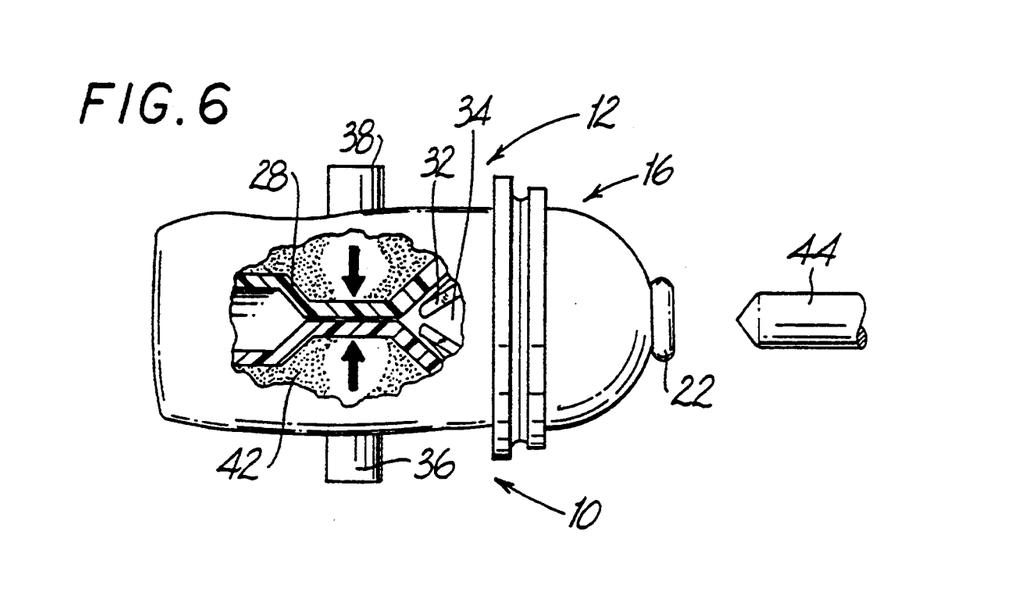
FIG. 6 is a side elevational partial cut-away view illustrating the valve assembly prior to insertion of a surgical instrument.
Figure 7:
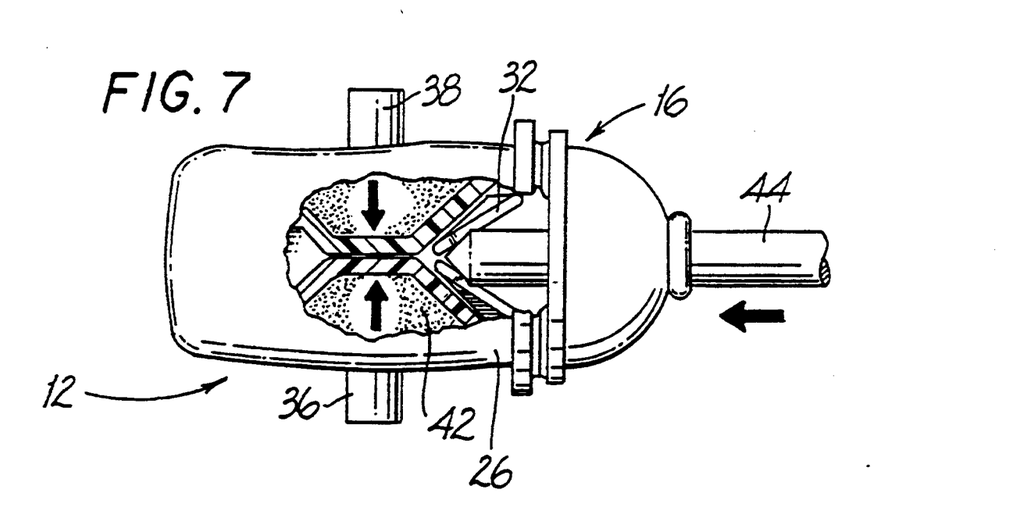
FIG. 7 is a side elevational partial cut-away view illustrating the valve assembly during insertion of a surgical instrument.
Figure 8:
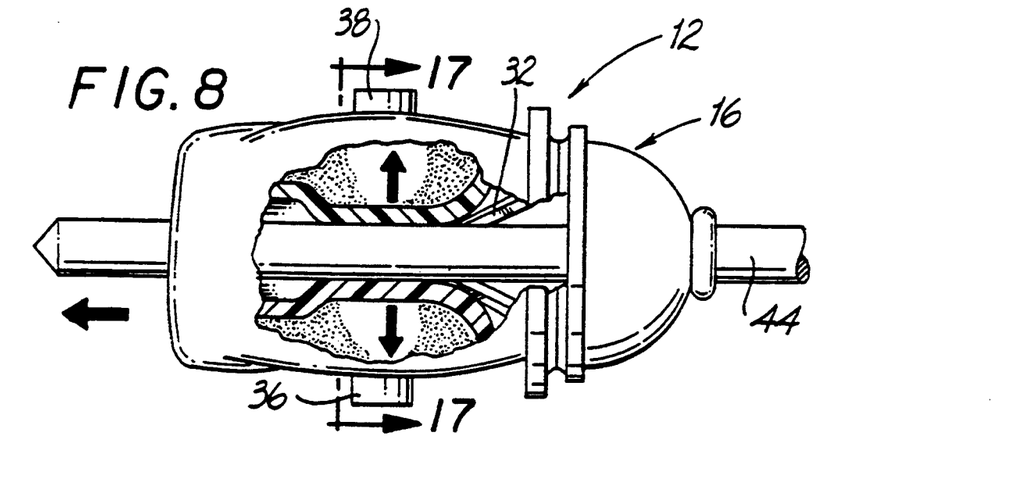
FIG. 8 is a side elevational partial cut-away view illustrating the valve assembly with a surgical instrument fully inserted.
Figure 9:
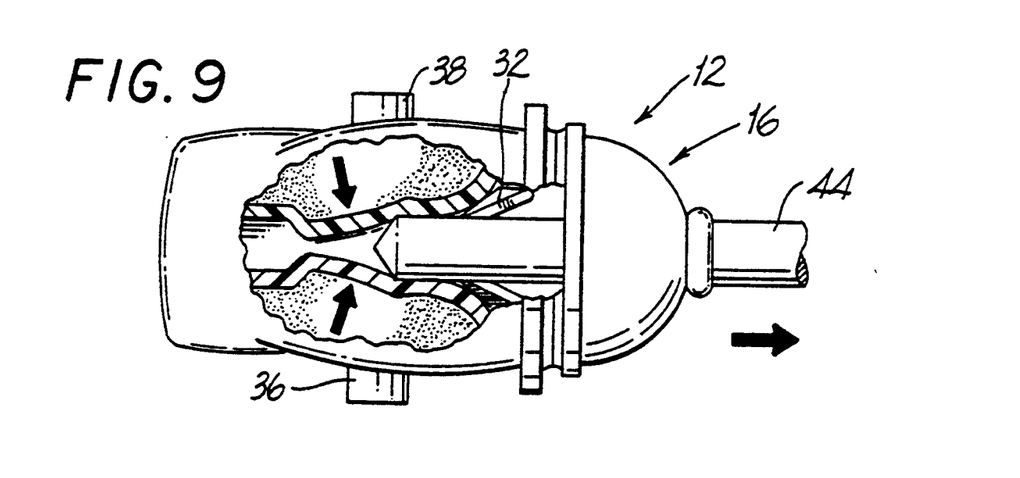
FIG. 9 is a side elevational partial cut-away view illustrating the valve assembly during removal of a surgical instrument.

As shown in FIGS. 4 and 5, the elongated substantially cylindrical distal portion 18 is folded onto itself and pulled proximally in the direction of the arrows. The distal edge 20 is affixed to the proximal wall plate 24 creating a cavity 40 by conventional techniques such as adhesives or heat sealing. Inlet port 36 is provided for injection of a gel 42, e.g., silicone, or like substance into cavity 40 while outlet port 38 provides a conduit for eliminating air from cavity 40. The gel 42 fills cavity 40 and provides longitudinal and radial pressure about the aperture 14 (FIG. 3). The gel 42 biases the middle portion 28 of aperture 14 closed, preventing gases and fluids from escaping through the body 12 when no instrument is present in the valve assembly 10. Similarly, the gel 42 biases the middle portion 28 of aperture 14 into fluid tight contact when an instrument is present in the aperture by longitudinally and radially providing pressure about the aperture 14 (FIG. 7). Valve assembly 10 is preferably incorporated into a cannula assembly of a trocar assembly similar to specific embodiments described herein below.

Aperture 14 is typically dimensioned less than or equal to the diameter of any instrument intended for entry into the proximal end of the body 12. Preferably, valve assembly 10 is fabricated from a material which is sufficiently flexible and resilient to accommodate and provide a seal about instruments of varying diameters, e.g., diameters of from 3 mm to 15 mm, and preferable diameters of from 5 mm to 12 mm.

Referring to FIGS. 6–9, a pointed obturator is shown approaching and entering valve assembly 10; however, any elongated relatively narrow instrument is contemplated. The valve assembly 10 accommodates the endoscopic portion of an instrument 44. The splines 32 engage the instrument 44 and protect the valve inner wall 34 at neck portion 26 while providing for the instrument's smooth entry into aperture 14 (FIG. 3). The middle portion 28 of the body portion 12 surrounds the instrument and provides longitudinal and radial pressure which substantially prevents gases or fluids from escaping from the body cavity when the instrument is inserted. The proximal opening 22 is of such a diameter to sealingly engage instrument 44 during insertion and withdrawal.

Figure 10:
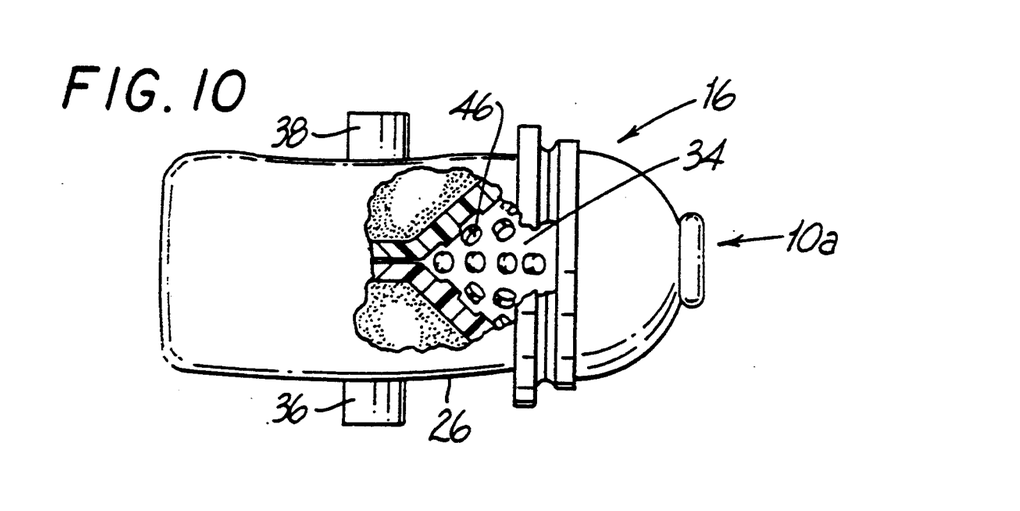
FIG. 10 is a side elevational partial cut-away view illustrating another embodiment of a valve assembly according to the present invention.

Another embodiment of the valve assembly 10 is shown in FIG. 10. The valve assembly 10a is similar to the previous embodiment shown in FIGS. 1–9, however, the embodiment shown in FIG. 10 includes a plurality of nubs 46, and the splines have been eliminated. The nubs 46 are positioned in the inner wall 34 of the neck portion 26 and extend outwardly from the inner wall 34. The nubs 46 engage the instrument during insertion of the instrument and minimize the risk of damage to the elastomeric inner wall, e.g., puncture thereof, by providing an intermediate surface between the instrument and the inner wall 34. The nubs are fabricated of the same elastic material as the valve assembly 10a and molded integrally with the valve body. The nubs 46 may also be fabricated of a different suitable flexible material.

Figure 11:
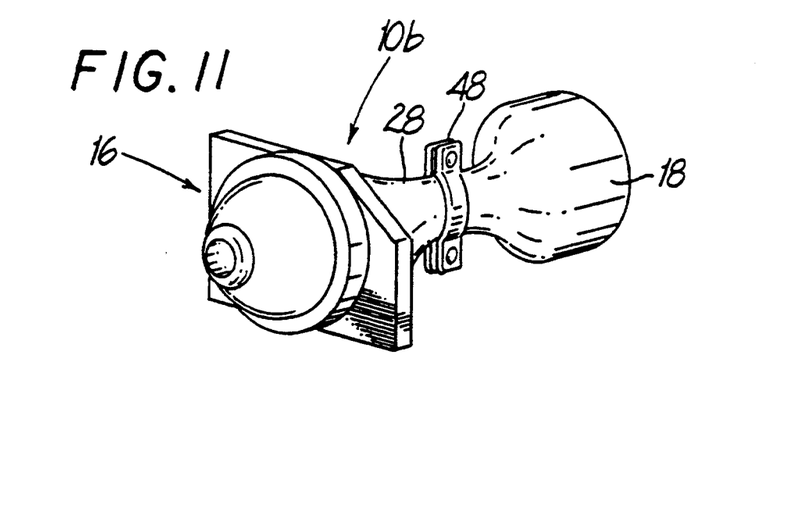
FIG. 11 is a perspective view illustrating another embodiment of a valve assembly according to the present invention.
Figure 12:
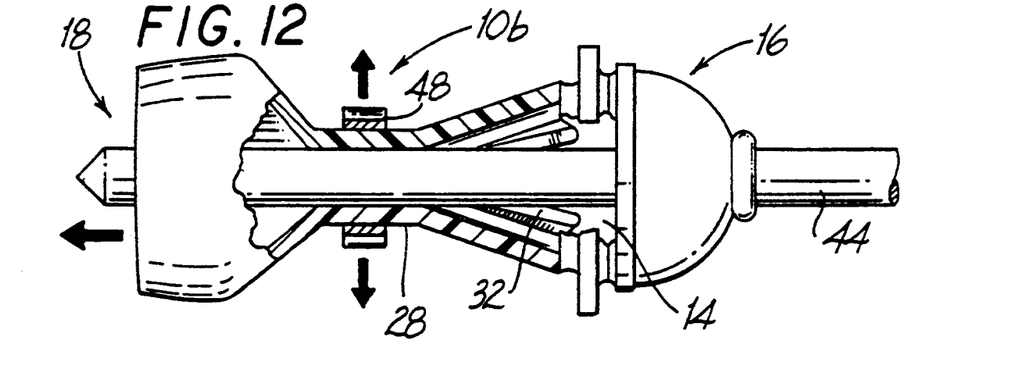
FIG. 12 is a side elevational partial cut-away view illustrating the valve assembly with an instrument fully inserted.
Figure 13:
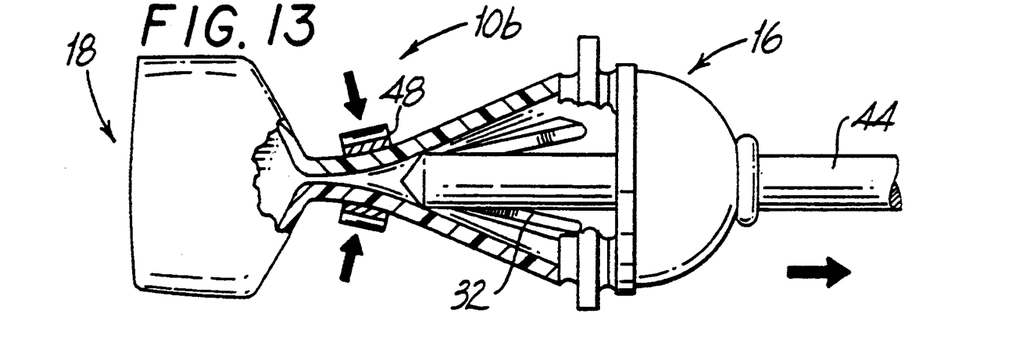
FIG. 13 is a side elevational partial cut-away view illustrating the valve assembly during withdrawal of the instrument.

Another embodiment of the valve assembly 10 is shown in FIGS. 11–13. The valve assembly 10b is similar to the previous embodiment shown in FIGS. 1–9, however, the embodiment shown in FIGS. 11–13 includes a collar 48 surrounding the middle portion 28 of the body 12. The collar 48 biases the middle portion of the central aperture 14 closed, inhibiting gases and fluids from escaping through the valve assembly 10b. When an instrument is present in the sealing valve aperture 14, the collar 48 forces the middle portion 28 to substantially surround the instrument and provides longitudinal and radial pressure to discourage any gases or fluids from escaping from the body cavity.

In operation, the splines 32 engage the instrument 44 and substantially protect the valve inner wall 34 as in the previous embodiment described above and illustrated in FIGS. 1–9. In the embodiment shown in FIGS. 11–13, the collar 48 which biases the middle portion 28 of the body 12 closed accommodates the entering instrument 44. The collar 48 urges the middle portion 28 inwardly to substantially surround the instrument and provides longitudinal and radial pressure which substantially discourages gases or fluids from escaping from the body cavity during insertion, utilization and extraction of the instrument 44 within the valve assembly 10b. Collar 48 may be constructed of any suitable material having resilient elastic properties, e.g., rubber.

Figure 14:
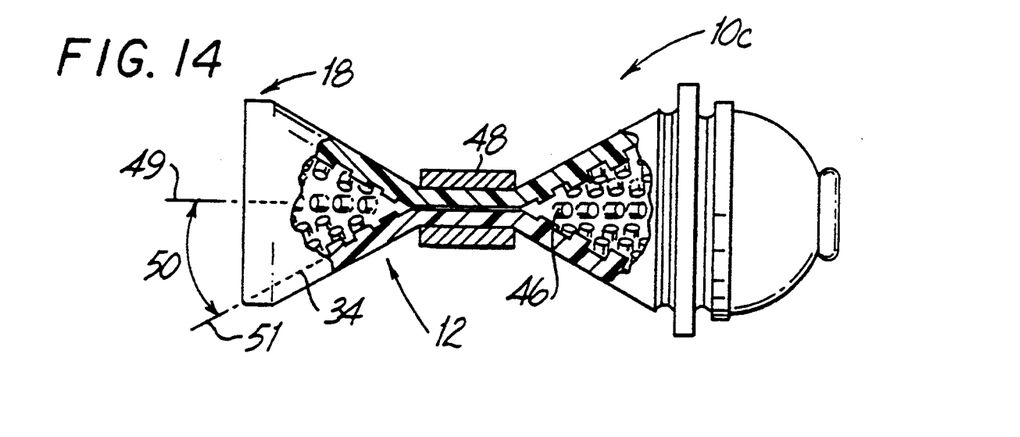
FIG. 14 is a side elevational partial cut-away view illustrating another embodiment of the valve assembly according to the present invention.
Figure 15:
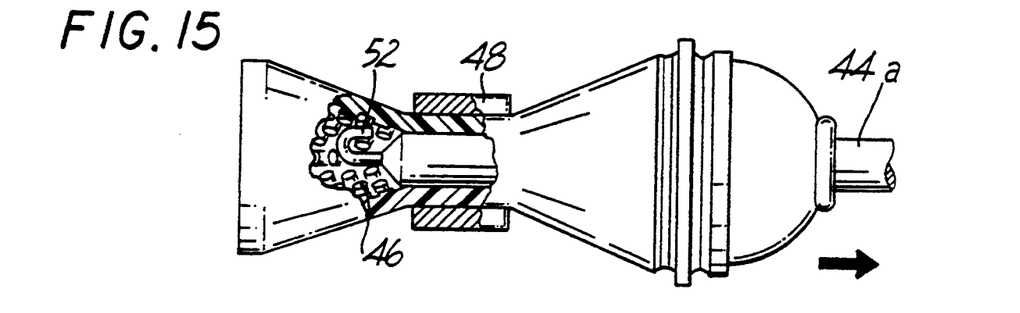
FIG. 15 is a side elevational partial cut-away view illustrating the valve assembly showing the clearance afforded an instrument at a distal end of the valve assembly.

Another embodiment of the valve assembly 10c is shown in FIG. 14–15, and is similar to previous embodiments shown in FIGS. 10, and 11–13. However, in the embodiment shown in FIGS. 14–15 the valve assembly 10c includes a distal end portion 18 which tapers outwardly at an angle 50. The angle 50 is defined by a longitudinal center line 49 and a line 51 in accord with the inner wall 34 of the body 12 when middle portion 28 is in its closed configuration, i.e., when collar 48 has biased aperture 14 closed. The angle is chosen to substantially discourage contact by an instrument, such as instrument 44a, having a hook 52, as shown in FIG. 15 from injuring, e.g., puncturing, or undesirably grabbing the inner wall 34 when the instrument 44a is being removed. The angle 51 is typically about 20° to 60°, preferably 30°.

Figure 16:
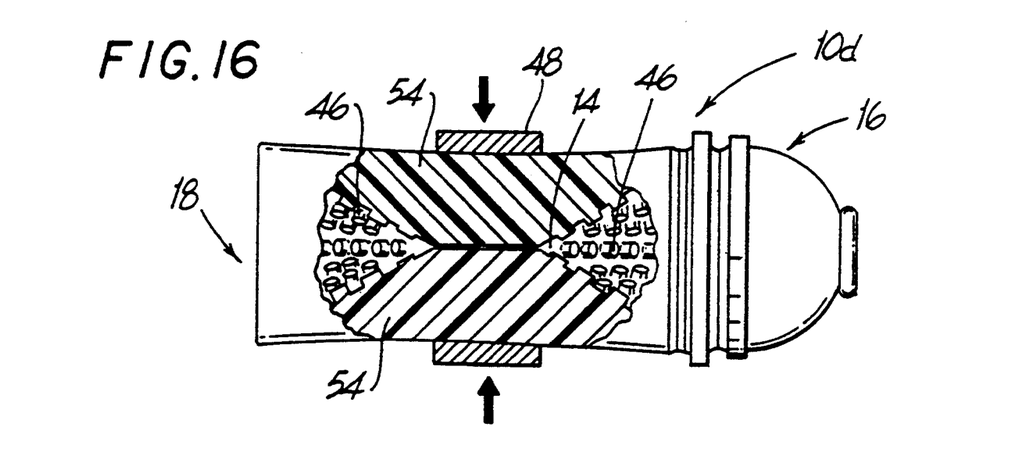
FIG. 16 is a side elevational partial cut-away view illustrating another embodiment of the valve assembly according to the present invention.

Another embodiment of the valve assembly 10d is shown in FIG. 16 and is similar to the previous embodiment shown in FIGS. 14–15. However, the embodiment shown in FIG. 16 has a generally cylindrical shape where the outside diameter of the valve assembly 10d is substantially constant. A substantially solid portion 54 enables the central aperture 14 to taper inwardly from the proximal and distal ends 16, 18 as in previous embodiments. Both the proximal and distal end inner wall 34 may include nubs 46, or splines 32 (not shown), and portion 54 may be further biased closed by a collar 48 or a similar biasing means if desired.

Figure 17:
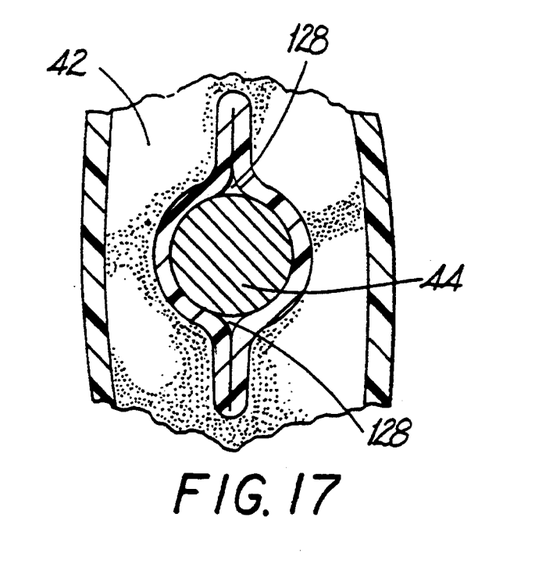
FIG. 17 is a cross-sectional view along line 17—17 of FIG. 8.
Figure 18:
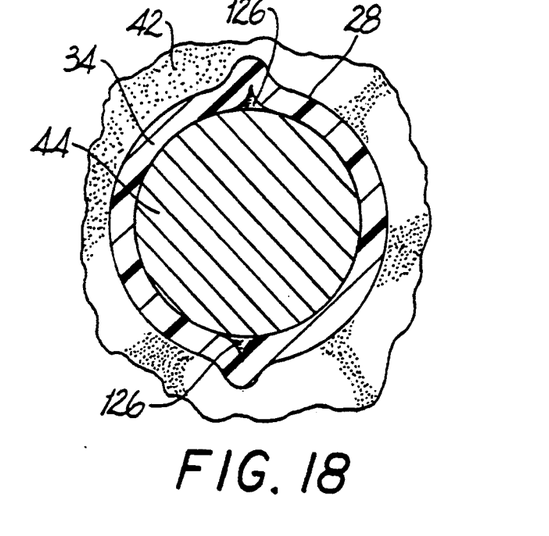
FIG. 18 is an enlarged cross-sectional view as shown in FIG. 17 illustrating a ridge used in accordance with the invention.
Figure 19:
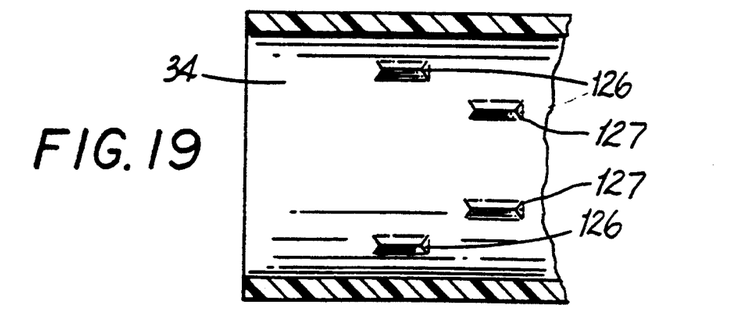
FIG. 19 is a cross-sectional view of another embodiment of the valve assembly of FIG. 18.

Another embodiment of a valve assembly 10 is illustrated in FIGS. 18–19 in which the middle portion 28 includes ridges 126 and 127 particularly placed to substantially fill a gap 128 which may occur as shown in FIG. 17 between the instrument 44 and the inner wall 34 after an instrument 44 of a lesser diameter than the unbiased aperture 14 is inserted. The resilient material of the valve 10 surrounds the instrument 44; however, when accommodating an instrument 44 smaller in diameter than the unbiased aperture 14 at the middle portion 28, the gap 128 forms at least at one side adjacent to the instrument between the instrument and the inner wall 34 as shown in FIG. 17. A properly placed ridge or set of ridges 126 or 127 on the inner wall 34 substantially fills the gap 128 as shown in FIG. 18.

A plurality of ridges or sets of ridges may be used as in FIG. 19 so that the gap 128 resulting from using different sized instruments 44, all of which are smaller in diameter than the unbiased central aperture 14, can be eliminated by the properly positioned ridges 126 or 127. The location of the ridge sets 126 and 127, and additional ridges as may be desired, may correspond to industry standardized instrument diameters such as 5 mm, 8 mm, 10 mm, and 12 mm.

More specifically, the ridges 126 may, for example, fill a gap 128 when an 8 mm diameter instrument is inserted through the valve assembly 10. Similarly, the ridges 127 may, for example, fill a gap 128 when a 5 mm diameter instrument is inserted through the valve assembly 10. Typically, the ridges or complementary pairs of ridges are axially spaced along middle portion 28.

Figure 20:
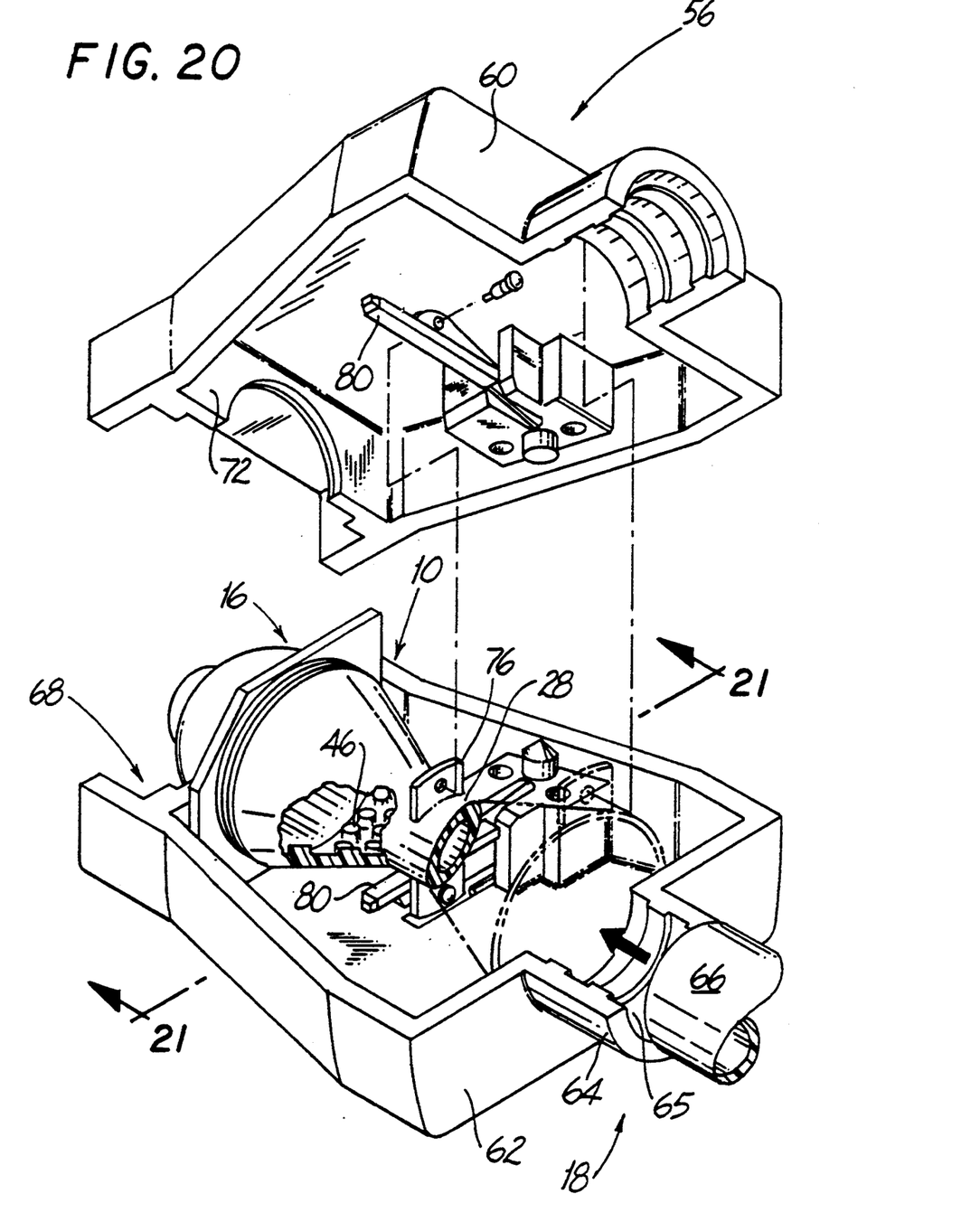
FIG. 20 is an exploded perspective view of a cannula of a trocar assembly illustrating the valve assembly in partial cut-away.
Figure 21:
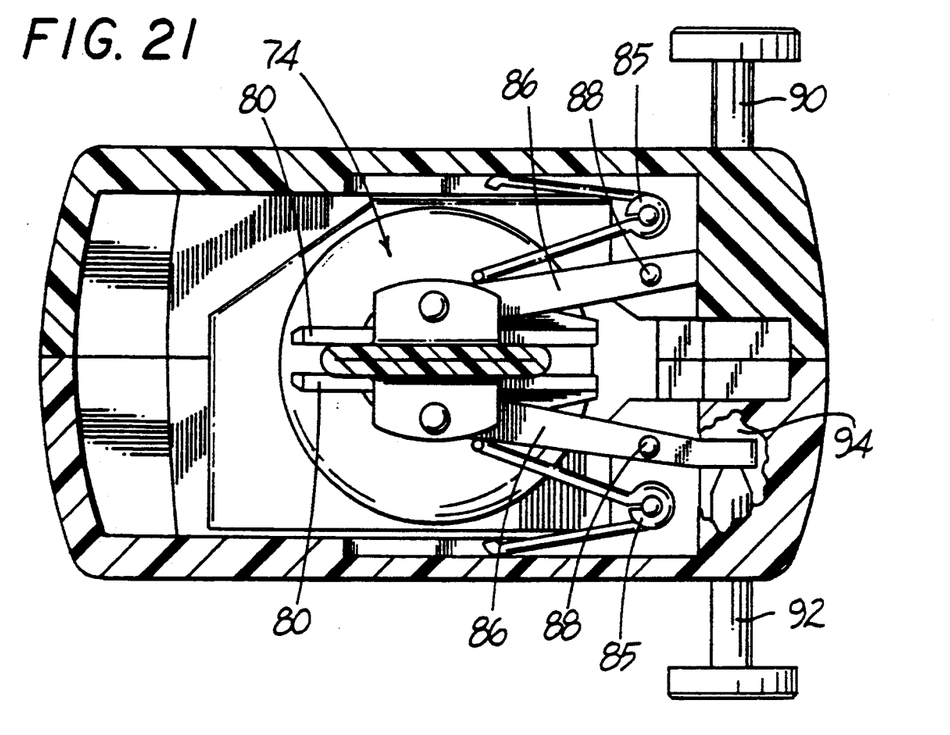
FIG. 21 is a cross-sectional view of a fully assembled cannula taken along lines 21—21 of FIG. 20 illustrating the valve assembly according to the present invention.

Preferably, the valve assembly 10 is incorporated in a cannula assembly 56 of a trocar assembly as best seen in FIG. 20 and FIG. 21. The valve assembly 10 is similar to the previous embodiment shown in FIGS. 14–15. The cannula assembly 56 includes a valve housing having an upper housing half section 60 and a lower housing half section 62, shown separated in FIG. 20 for convenience of illustration. The housing half sections 60, 62 are normally attached along the outer seam by suitable attachment techniques such as adhesive, ultrasonic welding, or the like.

The valve or cannula housing includes neck 64 at a distal end having an aperture 65 dimensioned for reception of an appropriate tube such as cannula 66. The cannula 66 is fabricated of a rigid material such as a plastic, fiberglass or metal. The proximal end of the valve housing 68 includes a partition 72 for stabilizing the valve assembly 10.

The lower housing half section 62 is shown with the upper housing half section 60 removed, so as to illustrate the novel valve assembly 10 of the present invention. The valve assembly 10 is shown partially cut away and in cross section for illustration purposes. Dual reciprocating securing members 74, as seen in FIG. 21, extends across the middle portion 28 of the body 12 as shown. The partition 72 holds the proximal end of the valve assembly 10 in position at plate 24 while the ear 76 affixed to middle portion 28 is connected to a corresponding clamp blade 80 for stabilizing the middle and distal end portions 28, 18 respectively. The partition 72 is constructed of the same relatively rigid plastic material as the valve housing such as polycarbonate, polyethylene or the like.

The valve assembly 10 includes clamp blades 80 which are connected to the inner surface of the lower housing half section 62 and the upper housing half section 60. Each clamp blade 80 is biased in a direction toward the other by a torsion spring 85 FIG. 21, having one leg in engagement with the adjacent housing wall and the other leg in engagement with a pivotal arm 86 FIG. 21, pivotally mounted at pivot pins 88. Each pivot arm 86 extends as shown, into the path of pins 90, 92 which are slidably mounted within bores 94.

The inner end of each pin 90, 92, FIG. 21 communicates with the appropriate pivotal arm 86 FIG. 21, such that manually depressing the slidable pins 90, 92 toward each other causes the pivot arms 86 to pivotally rotate away from each other. This motion causes the clamp blades 80 to separate allowing the middle portion 28 of the valve assembly 10 to open. When the pins 90, 92 are released, the middle portion 28 collapses to the configuration shown in FIG. 21 under action of the clamp blades 80 and the springs which provide a substantially gas tight seal between the proximal end 16 of the valve assembly 10 and the distal end 18. The sealing effect of the blades 80 on the valve assembly 10 is of sufficient gas tight character that pressurized gases used to insufflate a body cavity will not pass through the valve 10 when the instrument 44 is removed.

The pins 90, 92 may be selectively squeezed as desired by the surgeon to open the blades 80 to permit entry of the instrument through valve assembly 10, through the cannula 56 and into the body cavity. At this point, the tight contact between the instrument 44 and the inner wall 34 has sealed the inner body cavity from the outside atmosphere. This seal is provided by the resilient property of the stretched elastomeric material at middle portion 28 surrounding the aperture 14. Manipulation of the instrument 44 in any direction will not affect the seal, since the elastomeric material defining the aperture 14 will conform to the movements of the instrument and assume a shape necessary to maintain contact.

The aperture 14 is preferably dimensioned having a diameter between 3 and 15 mm to accommodate instruments such as clip appliers, laser tubes, photographic instruments, tubes or the like. However, depending upon need or application this dimensional range may be varied to accommodate any particular instrument.

Figure 22:
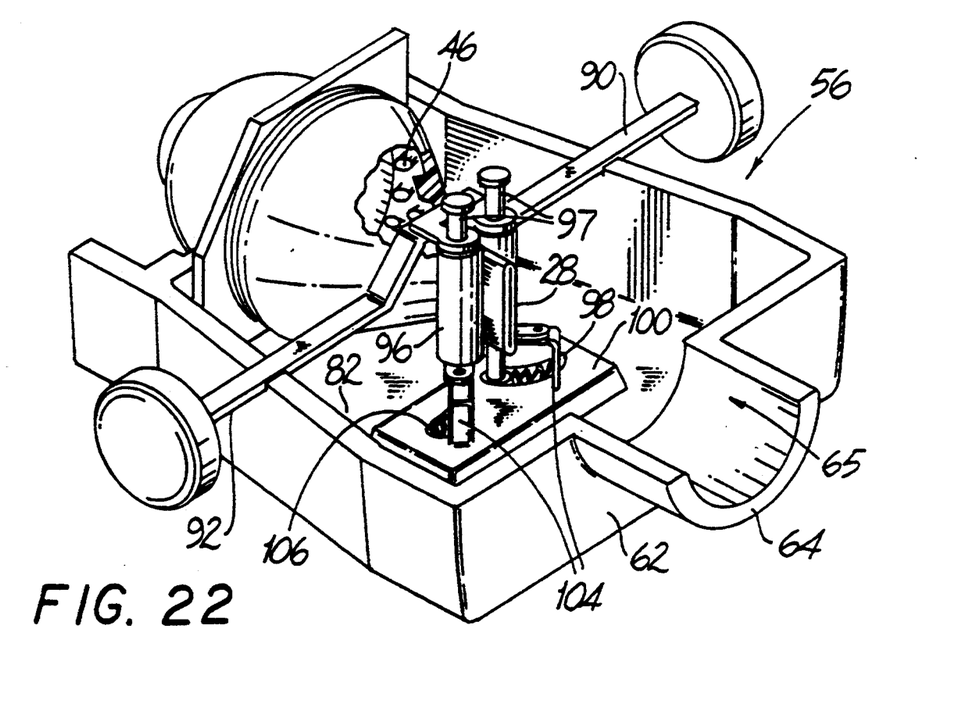
FIG. 22 is a perspective view in partial cut-away of another embodiment of the cannula of FIG. 20 illustrating the valve assembly according to the present invention.

Another embodiment of the cannula assembly 56 and valve assembly 10 is shown in FIG. 22, which is similar to the previous embodiment shown in FIG. 21. However in the embodiment shown in FIG. 22 the valve assembly includes generally cylindrical pinching members 96. A shaft 97 extends longitudinally through each member 96 and extends into a groove 98 in a plate 100 connected to the inner surface of the lower housing half section 62. The shaft 97 rides freely in the groove and is supported by a support bar 104 attached to the plate 100. A spring 106 positioned in the groove 98 biases the shaft 97, and thus member 96 to the position shown at one end of the groove 98. Member 96 biases the middle portion 28 of the valve assembly 10 in the closed position substantially preventing gases from entering or exiting. Actuation levers 90, 92, positioned in this embodiment perpendicular to levers 90, 92 in FIG. 21, provide manual mechanical activation of members 96 to open valve assembly 10.

In operation, upon insertion of an instrument into the proximal end of the valve housing 68 and the proximal end of the valve assembly 10, the nubs 46 engage the instrument providing substantial protection to the inner wall 34. Members 96 are moved in response to actuation of levers 90 and 92, and shafts 97 respond by moving in their corresponding grooves 98. Middle portion 28 of valve assembly 10 provides longitudinal and radial pressure in conjunction with members 96 to the instrument, thus providing and maintaining a substantial gas tight seal.

Figure 23:
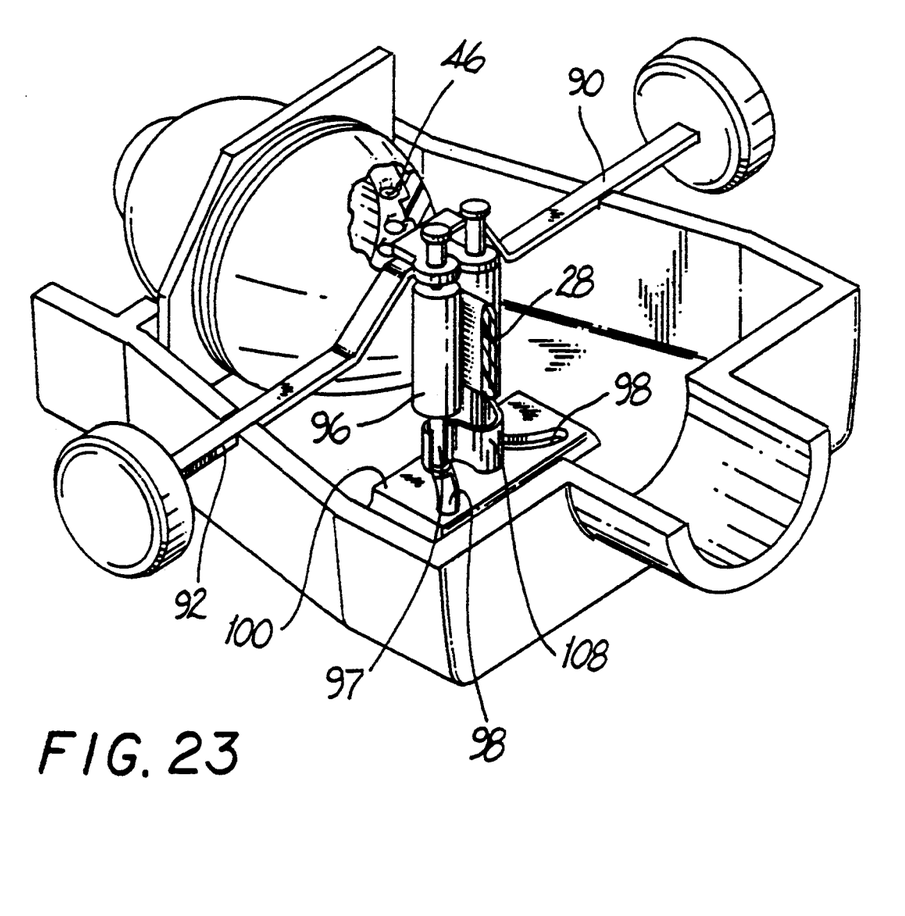
FIG. 23 is a perspective view in partial cut-away of the cannula of FIG. 22 illustrating another embodiment of the biasing means for the valve assembly.

Another embodiment of the valve assembly and cannula assembly is shown in FIG. 23 and is similar to the previous embodiment shown in FIG. 22. However, in the embodiment shown in FIG. 23 the valve assembly includes a resilient member 108 biased in a generally "U" shaped configuration which replaces springs 106. The resilient member 108 is attached to the bottom portion of the shafts 97 and biases shafts 97, and thereby members 96, in the closed position. The embodiment shown in FIG. 23 operates similar to the embodiment shown in FIG. 22.

Figure 24:
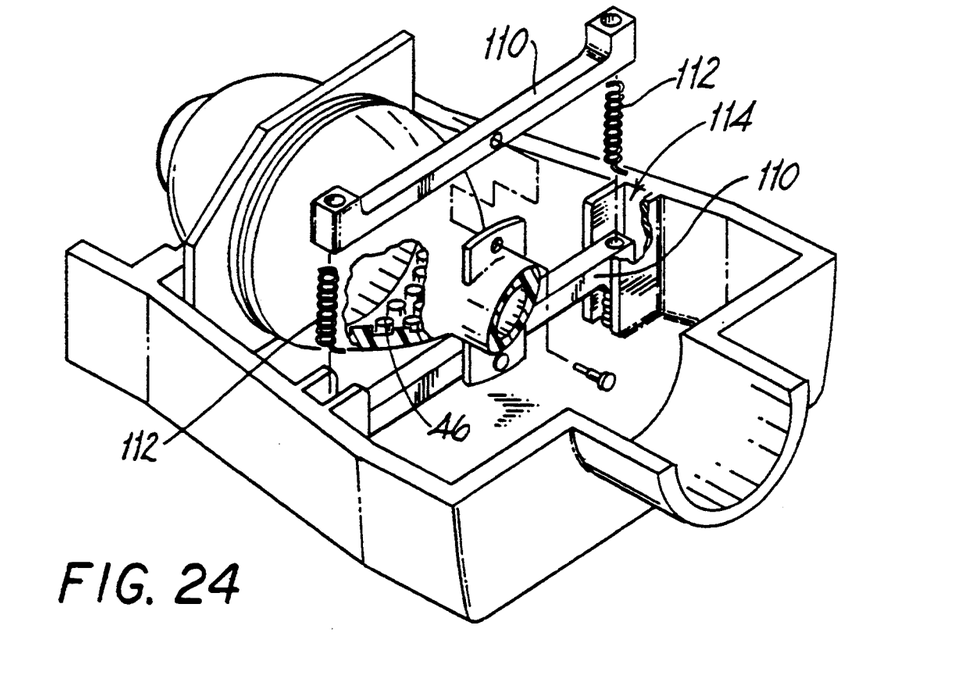
FIG. 24 is a perspective view in partial cut-away of the cannula of FIG. 22 illustrating another embodiment of the biasing means for the valve assembly.

Another embodiment of the cannula assembly 56 and the valve assembly 10 is shown in FIG. 24, and is similar to previous embodiments shown in FIGS. 22 and 23, except for the provision of parallel bars 110 which are positioned in the lower and upper half sections 62 and 60 of the cannula housing 56 substantially about the middle portion 28 of the valve assembly 10. The bars 110 are biased towards each other by springs 112 attached at their distal ends and aligned in grooves 114. In operation, when an instrument is inserted into the cannula assembly 56 and into the valve assembly 10 the biased bars 110 move in the grooves 114 against the biasing of the springs and maintain a gas tight seal about the instrument.

Figure 25:
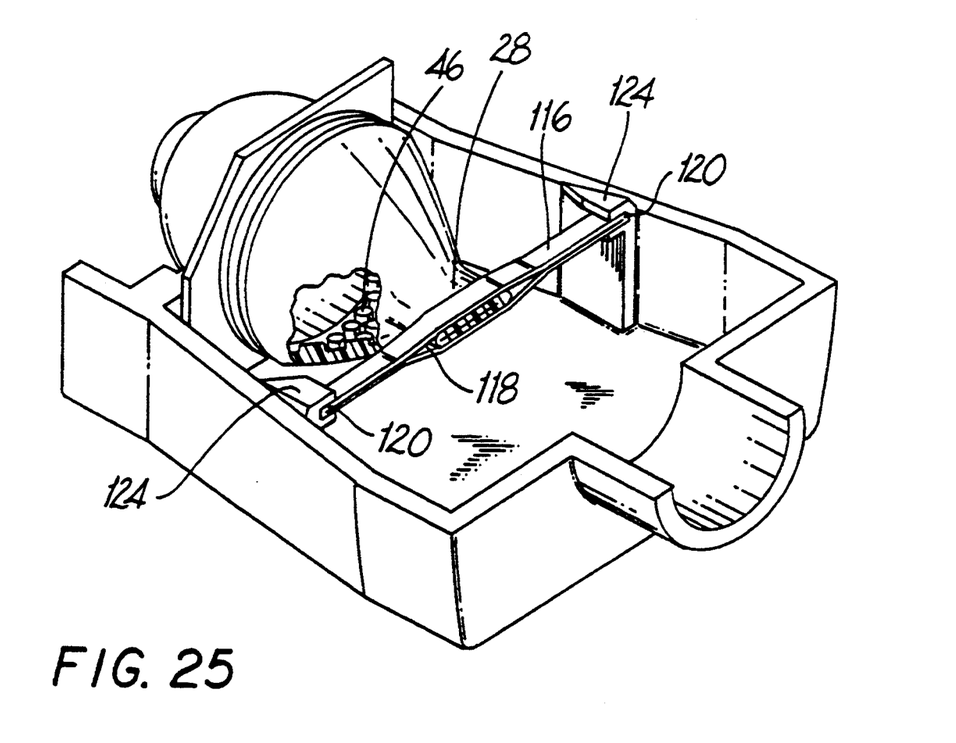
FIG. 25 is a perspective view in partial cut-away of the cannula of FIG. 22 illustrating another embodiment of the biasing means for the valve assembly.

Another similar embodiment of the cannula assembly 56 and the valve assembly 10 is shown in FIG. 25. In this embodiment, the valve assembly 10 includes a resilient one piece bar 116 having an opening in a middle segment 118 to accommodate the middle portion 28 of valve assembly 10. The opposite distal ends 120 of the resilient bar 116 are connected to the side wall receptacles 124. Of course, bar 116 may be constructed of two members overlapping each other.

When an instrument is inserted into the cannula assembly 56 and into the valve assembly 10 the resilient bar 116 accommodates the instrument, while assisting valve assembly 10 in providing longitudinal and radial pressure about the instrument to maintain a fluid tight seal.

When the valve assembly 10 is used as part of a cannula assembly 56 as in the present embodiment of FIGS. 20-25, an obturator of the trocar assembly is fitted within the cannula assembly and used to insert the cannula into a body cavity by first penetrating the cavity wall. Thereafter, the obturator is removed, permitting insertion of instruments into the patient's body through the cannula to perform the desired procedure. Thus, the significance of providing control to the surgeon over an assuredly sealed cannula valve assembly cannot be over-emphasized. For laparoscopic procedures the valve assembly will prevent leakage of gases to maintain insufflation of the cavity during the surgical procedures.

Figure 26:
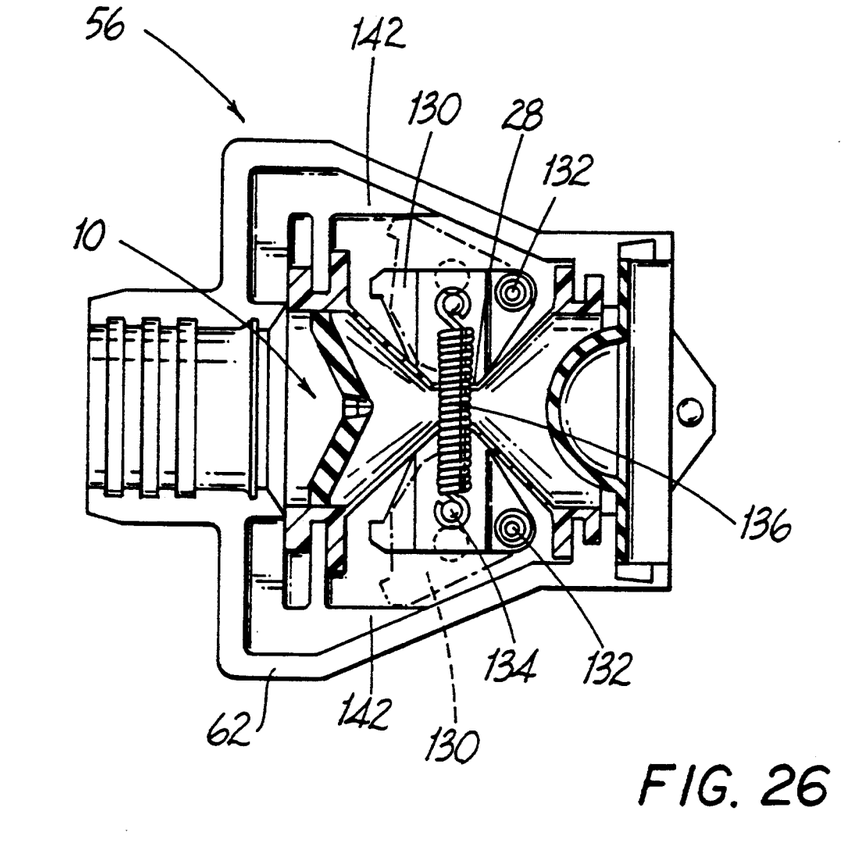
FIG. 26 is a top view in partial cut-away of the cannula of FIG. 22 illustrating another embodiment of the biasing means for the valve assembly.
Figure 27:
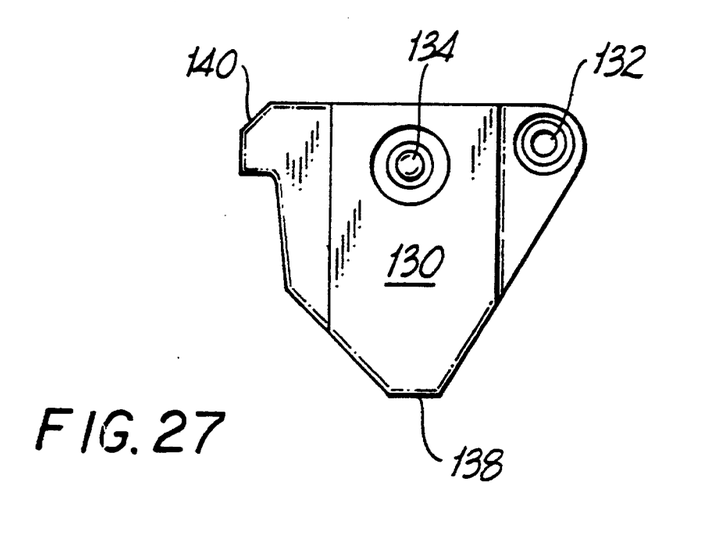
FIG. 27 is a top view of a cam used in accordance with the embodiment of FIG. 26.

Another embodiment of the valve assembly 10 positioned in a cannula assembly 56 is shown in FIGS. 26 and 27 and is similar to the previous embodiments shown in FIGS. 21-25. However, in the embodiment shown in FIGS. 26 and 27 the valve assembly 10 preferably includes a pair of pivotable cams 130 positioned in the lower half section 62 of the cannula housing 56. The cams 130 act as biasing means for biasing the middle portion 28 of the valve assembly 10 closed prior to instrument insertion into the valve assembly 10, and for biasing middle portion 28 against the outer surface of an inserted instrument.

Each cam 130 includes a pivot point 132 at a proximal end and an attachment portion 134 for coupling with an actuating spring 136. The cams 130 further include contact faces 138 and stop surfaces 140. The cams 130 are positioned on opposite sides of the middle portion 28 and are biased towards one another by the actuation spring 136, thus, the cams 130 work in concert to bias closed the middle portion 28 of the valve assembly 10 between them.

In operation, prior to instrument insertion in the valve assembly 10, the actuating spring biases the cams 130 towards one another thereby biasing closed the middle portion 28 of the valve assembly 10 and providing a substantially gas tight seal. After instrument insertion into the valve assembly 10, the cams 130 pivot at their proximal pivot points 132 and rotate distally against the biasing action of the actuation spring 136 assuming the position shown by the dotted lines in FIG. 26. The cams 130 encourage the middle portion 28 of the valve assembly 10 to engage the outer surface of the inserted instrument and, thereby, the valve assembly 10 provides and maintains a substantially gas tight seal. Lastly, the stop surfaces 140 contact a side wall 142 of the lower half section 62 of the cannula housing 56 when the cams 130 are fully rotated.

The valve assembly described above in the preferred embodiments and illustrated in the accompanying drawings is preferably capable of accommodating instruments varying in diameter of from 3 mm to 15 mm, and preferably for diameters of from 5 mm to 12 mm. When inserting the instrument into the valve assembly as described in the above embodiments and illustrated in the accompanying drawings, the insertion force, i.e., the axial force asserted against the instrument to pass the instrument into and through the valve assembly is preferably kept to a minimum. For example, preferable insertion forces of approximately no more than 5 pounds are desirable for instruments having approximate diameters of more than 9 mm. Insertion forces of approximately no more than 4 pounds are desirable for instruments having approximate diameters of between 5 mm and 8 mm.

Moreover, preferable insertion forces of approximately 7 pounds are desirable for instruments having approximate diameters of 9 mm to 15 mm. Insertion forces of approximately no more than 6 pounds are desirable for instruments having approximate diameters of between 10 mm and 12 mm.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A valve assembly for sealing an incision in a patient's body and adapted for introduction of surgical instruments into the patient's body comprising:
   a cylindrical valve body having a proximal and distal end, said cylindrical valve body further including an inner wall and an outer wall defining a cavity therebetween, said inner wall forming an aperture passing through said valve body;
   means associated with said inner wall of said cylindrical valve body for facilitating passage of an instrument through said aperture, said facilitating means including a plurality of rib members positioned on an inner wall of said valve body radially extending into said aperture adjacent at least said proximal end of said body to engage an instrument inserted into said aperture to substantially prevent contact between said instrument and said inner wall of said valve body; and means to bias at least a portion of said valve body to a configuration whereby said aperture is closed to form a substantially gas tight seal prior to inserting an instrument therethrough.

2. A valve assembly according to claim 1, wherein said inner wall tapers inwardly and said outer wall has a generally cylindrical shape.

3. A valve assembly according to claim 1, wherein said biasing means comprises a fluid substantially filling said cavity.

4. A valve assembly according to claim 1, wherein said biasing means biases said inner wall.

5. A valve assembly according to claim 1, wherein said inner wall defines an inwardly tapering aperture from said proximal end of said valve body towards said distal end.

6. A valve assembly according to claim 5, wherein said cylindrical valve body includes a proximal end, a middle portion and a distal end configured and dimensioned such that said inner wall of said cylindrical body tapers at said middle portion such that said cylindrical valve body has a lesser diameter at said middle portion than at said distal and proximal ends.

7. A valve assembly according to claim 1, wherein said valve body is formed of flexibly resilient material, and said inner wall is configured and dimensioned such that insertion of the instrument into said aperture will cause the inner wall to resiliently engage the outer surface of the instrument in a substantially gas tight manner.

8. A valve assembly according to claim 1, wherein said rib members extend longitudinally from said proximal end of said valve body.

* * * * *